(12) United States Patent
Yaffe

(10) Patent No.: US 10,898,289 B2
(45) Date of Patent: Jan. 26, 2021

(54) DEVICES AND METHODS FOR PARTLY ISOLATING A TARGET BIOLOGICAL STRUCTURE

(71) Applicant: Verily Life Sciences LLC, South San Francisco, CA (US)

(72) Inventor: Benjamin K. Yaffe, San Francisco, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 101 days.

(21) Appl. No.: 16/230,337

(22) Filed: Dec. 21, 2018

(65) Prior Publication Data

US 2019/0201154 A1 Jul. 4, 2019

Related U.S. Application Data

(60) Provisional application No. 62/611,244, filed on Dec. 28, 2017.

(51) Int. Cl.
*A61B 90/00* (2016.01)
*A61B 17/02* (2006.01)
*A61B 17/00* (2006.01)
*A61B 17/12* (2006.01)

(52) U.S. Cl.
CPC .............. *A61B 90/08* (2016.02); *A61B 17/02* (2013.01); *A61B 17/0218* (2013.01); *A61B 2017/00283* (2013.01); *A61B 2017/00557* (2013.01); *A61B 2017/00946* (2013.01); *A61B 2017/0212* (2013.01); *A61B 2017/12004* (2013.01); *A61B 2090/036* (2016.02); *A61B 2090/0815* (2016.02); *A61B 2090/0817* (2016.02); *A61B 2090/08021* (2016.02)

(58) Field of Classification Search
CPC ...... A61B 90/08; A61B 17/02; A61B 17/0218
USPC .......................................................... 600/37
See application file for complete search history.

(56) References Cited

U.S. PATENT DOCUMENTS

| | | |
|---|---|---|
| 4,841,948 A | 6/1989 | Bauer et al. |
| 5,383,889 A | 1/1995 | Warner et al. |
| 5,439,476 A | 8/1995 | Frantzides |
| 2003/0004473 A1 | 1/2003 | Bonadio et al. |
| 2017/0360590 A1 | 12/2017 | Corrigan et al. |

OTHER PUBLICATIONS

International Search Report and Written Opinion for International Application No. PCT/US2018/067259, dated Mar. 13, 2019, 16 pages.
International Application No. PCT/US2018/067259, International Preliminary Report on Patentability, dated Jul. 9, 2020, 11 pages.

*Primary Examiner* — John P Lacyk
(74) *Attorney, Agent, or Firm* — Kilpatrick Townsend & Stockton LLP

(57) ABSTRACT

The present disclosure relates to devices and methods for partly isolating a target biological structure. The device may include a main body comprising a front face and a rear face, the main body having a proximal end and a distal end. The distal end may be arcuate in a first state and may be substantially planar in a second state. The device may further include one or more balloons disposed on the distal end of the main body. Each of the one or more balloons is deflated in the first state and each of the one or more balloons is inflated in the second state. The distal end of the main body is configured to deform to be substantially planar when each of the one or more balloons are inflated in the second state.

19 Claims, 9 Drawing Sheets

DEVICES AND METHODS FOR PARTLY ISOLATING A TARGET BIOLOGICAL STRUCTURE

CROSS-REFERENCE TO RELATED APPLICATION

This application claims the benefit of and the priority to U.S. Provisional Application No. 62/611,244, filed on Dec. 28, 2017, which is hereby incorporated by reference in its entirety for all purposes.

FIELD OF THE INVENTION

The present disclosure generally relates to devices for partly isolating a target biological structure, and more specifically relates to atraumatic devices and methods for partly isolating and supporting a target biological structure that provides multidirectional access to the target biological structure.

BACKGROUND

Laparoscopic surgery is traditionally conducted through a series of small incisions in a patient, e.g., in the patient's abdomen. In laparoscopic procedures, biological structures, e.g., the splenic artery, are often found next to other vasculature, neural tissue, or organs. Often times, surgeries require modification, ligation, incision, or attachment of tools to one of these biological structures. Currently, these procedures may be performed with balloon dissection tools to separate tissue at natural tissue plane boundaries. The tissues may be retracted by gross retractor tools or by silicone vessel retractors that may cause trauma to the surrounding structures. Therefore, less traumatic devices and techniques are needed for these laparoscopic procedures.

SUMMARY

In some embodiments, the present disclosure relates to device for partly isolating a target biological structure in a patient. The device may include a main body comprising a front face and a rear face, the main body having a proximal end and a distal end. The distal end may be arcuate in a first state and may be substantially planar in a second state. The device may further include one or more balloons disposed on the distal end of the main body. Each of the one or more balloons is deflated in the first state and each of the one or more balloons is inflated in the second state. The distal end of the main body is configured to deform to be substantially planar when each of the one or more balloons are inflated in the second state. In one aspect, the device may further include an additional balloon on the rear face of the main body and the additional balloon may be a hemostatic balloon. In another aspect, the one or more balloons comprise a first balloon on a first side of the main body and a second balloon on a second side of the main body. In the second state, a channel exists between the first balloon and the second balloon. In the second state, the first balloon and the second balloon support a target biological structure above the front face of the main body, and the channel is located below the target biological structure.

In another embodiment, the present disclosure relates to a method. The method may include making an incision in a patient, inserting a device, in a first state, to access the target biological structure in the patient through the incision, positioning the device at least partially beneath a target biological structure in the patient, and transitioning the device from the first state to the second state. The device may include a main body comprising a front face and a rear face, the main body having a proximal end and a distal end. The distal end may be arcuate in a first state and may be substantially planar in a second state. The device may further include one or more balloons disposed on the distal end of the main body. Each of the one or more balloons is deflated in the first state and each of the one or more balloons is inflated in the second state. The distal end of the main body is configured to deform to be substantially planar when each of the one or more balloons are inflated in the second state. In the transitioning step, each of the one or more balloons are at least partly inflated and the target biological structure is at least partly supported by each of the one or more balloons.

In another embodiment, the present disclosure relates to a device for positioning a target biological structure in a patient. The device may include a base plate comprising a front face and a rear face, the base plate having proximal and distal ends. The base plate includes a first sidewall disposed on a first end of the front face and a second sidewall disposed on an opposing second end of the front face. A channel exists between the first sidewall and the second sidewall. The base plate may include an end wall positioned on the distal end of the base plate between the first sidewall and the second sidewall. The end wall is inclined relative to the proximal end of the base plate. In one aspect, the first sidewall, the second sidewall, and the end wall each have a constant height defining an area of the channel, wherein a target biological structure is supported on the first sidewall and the second sidewall. In another aspect, each of the first sidewall and the second sidewall comprises a recess on a portion of a surface of each of the first sidewall and the second sidewall that is opposing the front face of the base plate.

In another embodiment, the present disclosure relates to a method. The method may include making an incision in a patient, inserting a device to access a target biological structure in the patient through the incision, and positioning the device at least partially beneath the target biological structure in the patient. The device may include a base plate comprising a front face and a rear face, the base plate having proximal and distal ends. The base plate includes a first sidewall disposed on a first end of the front face and a second sidewall disposed on an opposing second end of the front face. A channel exists between the first sidewall and the second sidewall. The base plate includes an end wall positioned on the distal end of the base plate between the first sidewall and the second sidewall. The end wall is inclined relative to the proximal end of the base plate. The target biological structure is at least partly supported on the first sidewall and second sidewall above the base plate. In one aspect, the rear face of the base plate may include a conduit configured to receive a guidewire. The step of positioning the device comprises threading the device over the guidewire to the target biological structure.

These illustrative embodiments are mentioned not to limit or define the scope of this disclosure, but rather to provide examples to aid understanding thereof. Illustrative embodiments are discussed in the Detailed Description, which provides further description. Advantages offered by various embodiments may be further understood by examining this specification.

BRIEF DESCRIPTION OF THE DRAWINGS

The accompanying drawings, which are incorporated into and constitute a part of this specification, illustrate one or more certain embodiments and, together with the description of the embodiments, serve to explain the principles and implementations of the certain embodiments.

DETAILED DESCRIPTION

Figure 1:
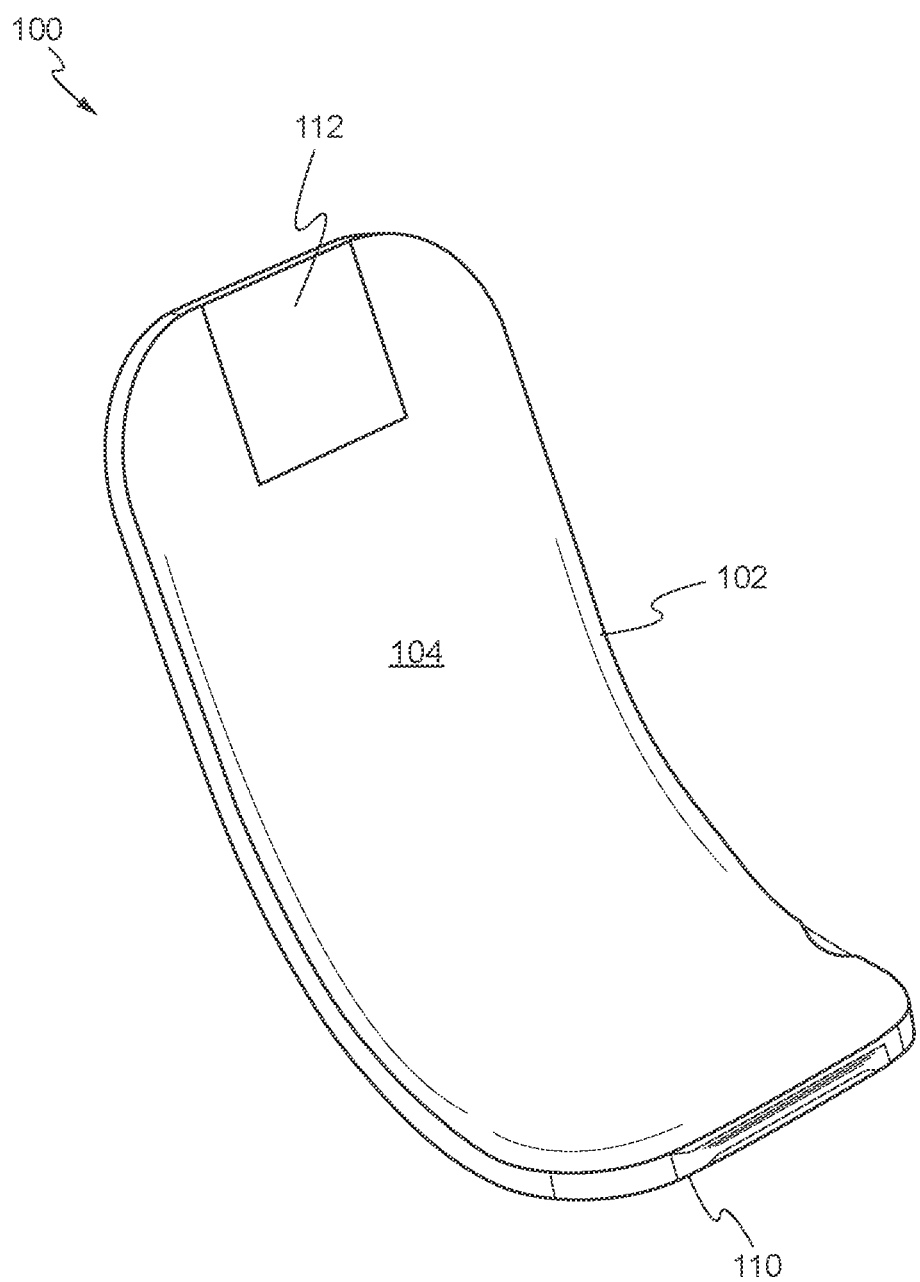
FIG. 1 shows a front perspective view of a device according to one embodiment of the present invention.

Those of ordinary skill in the art will realize that the following description is illustrative only and is not intended to be in any way limiting. Reference will now be made in detail to implementations of embodiments as illustrated in the accompanying drawings. The same reference numerals will be used throughout the drawings and the following description to refer to the same or like items.

The present disclosure relates to devices that allow a user to partly isolate and access a target biological structure in a patient. As used herein, the phrase "target biological structure" refers to any type of vasculature, artery, tissue, or organ. As used herein, the term "patient" refers to any multicellular organism, e.g., an animal (e.g., a human).

In the illustrative embodiments discussed below, the devices may be discussed in the context of positioning an artery from a neurovascular bundle near the pancreas. However, the devices and methods disclosed herein can be used in any laparoscopic procedure. The devices enable a user to partly isolate, i.e., pull away or separate, a target biological structure from surrounding structures, without causing trauma to the surrounding structures or the target biological structure. The device also supports the target biological structure in a manner that provides multidirectional access to areas of the target biological structure.

In some embodiments, the devices may be used during laparoscopic procedures. Laparoscopic surgery may performed through very small incisions in the abdomen of the patient, generally to provide access for a trocar or a cannula device. After incision, the abdomen of a patient may be insufflated with gas in order to expand the abdominal cavity to provide a space to perform laparoscopy. In this example, the devices may be inserted through the small incision to enable a user, e.g., a surgeon, to position and support a target biological structure thereon. While the target biological structure is supported on the device, the user can manipulate, e.g., modify, ligate, incise, or attach tools to, the target biological structure.

Devices

Figure 2:
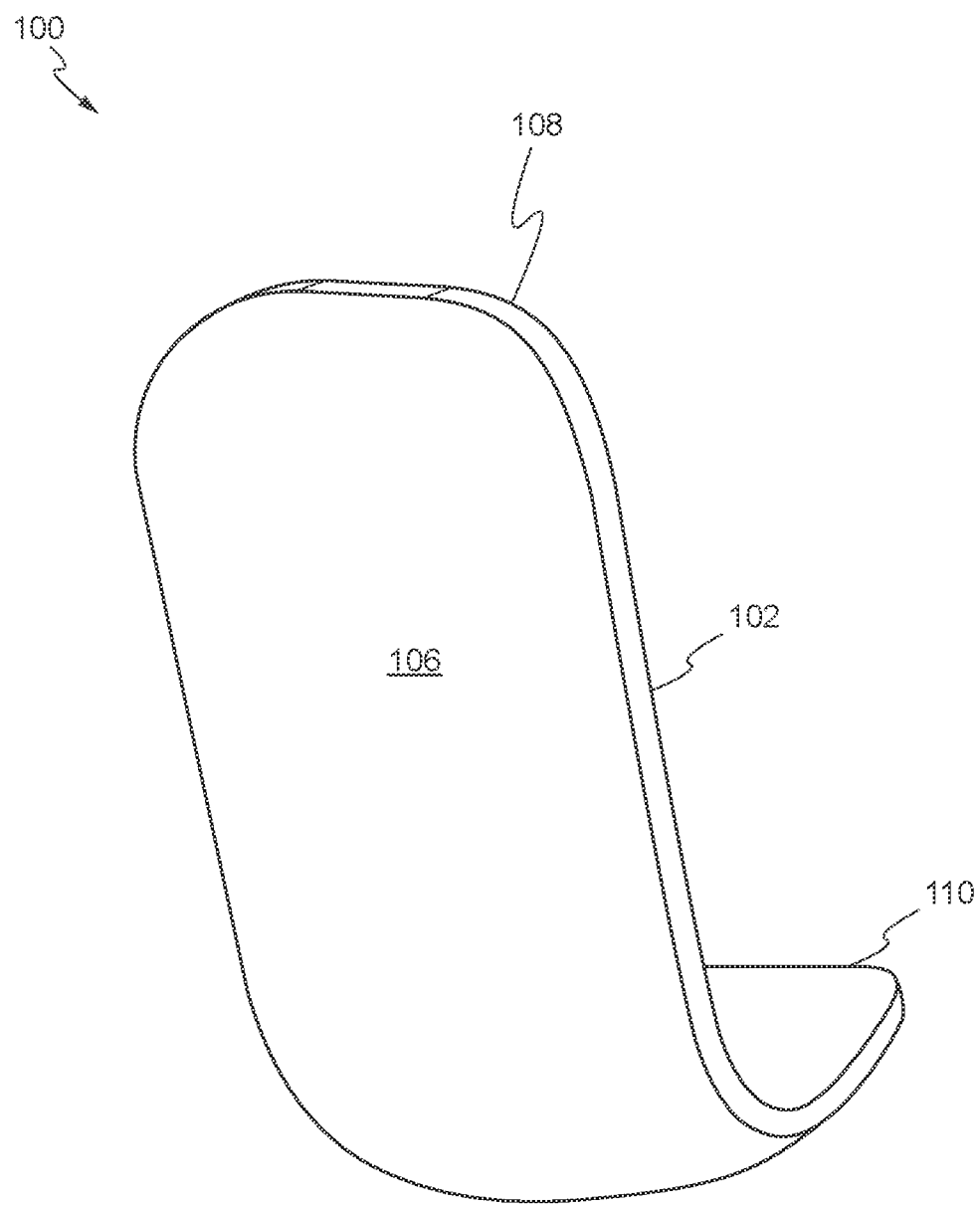
FIG. 2 shows a rear perspective view of the device according to one embodiment of the present invention.

FIGS. 1 and 2 show a front perspective view and a rear perspective view of a device, respectively, according to one embodiment of the present invention. The device 100 may comprise a main body 102 including a front face 104 and a rear face 106. The main body 102 has a proximal end 108 and a distal end 110. The distal end 110 of the main body 102 is substantially arcuate. As used herein, the term "proximal end" refers to a first end of the main body, while the term "distal end" refers to a second end opposing the first end. For example, the proximal end may be an end of the main body which is closest to the user and the distal end may be an end of the main body which is furthest from the user.

The proximal end 108 of the main body 102 is substantially flat and planar with respect to the distal end 110. In some embodiments, the proximal end 108 may include a handle 112. The handle 112 may be removably attached to the proximal end 108. In some embodiments, the handle 112 may be an articulating handle. In use, the user can grasp the handle 112 of the device 100 using hemostatic pliers. In other embodiments, the handle 112 can include a throughhole to thread a suture to function as a retention string. In other embodiments, the handle 112 can be provided on the distal end 110 of the main body 102.

The distal end 110 of the main body 102 is substantially arcuate, i.e., the distal end 110 has a curvature transverse to the longitudinal axis of the proximal end 108. For example, arcuate may refer to the distal end 110 being shaped or bent in the form of an arc or bow with respect to the proximal end 108 of the main body 102. In some embodiments, the distal end 110 may have a constant curvature. In other embodiments, the distal end 110 may have varying degrees of curvature. The distal end 110 enables the device 100 to pull away and isolate the target biological structure from surrounding structures. For example, the distal end 110 can be positioned in a manner to lift and separate the target biological structure from surrounding tissue. In some embodiments, the distal end 110 of the device 100 can be used to separate the splenic artery from a neurovascular bundle adjacent to the pancreas.

In some embodiments, the distal end 110 is deformable, such that the distal end 100 deforms in response to a sufficient force applied to the distal end 110. In particular, the distal end 110 is capable of deforming from an applied force to adjust the curvature of the distal end 110. In this way, the curvature of the distal end 110 can be adjusted for different procedures. Initially, the distal end 110 is arcuate. The distal end 110 of the main body 102 can be sufficiently curved with beveled edges such that it does not cause trauma to surrounding structures. For example, the corners of the distal end are rounded.

The device 100 may be formed of a flexible polymer material, e.g., a thermoplastic polymer. For example, the device 100 can be formed of a firm, lightweight, plastic material such as, polyether ether ketone (PEEK) or polyurethane. The device 100 can also be formed of other flexible medical grade plastic materials. In some embodiments, the device may be formed of a malleable metal, e.g., stainless steel or aluminum. In other embodiments, the device 100 is formed of a rigid material such that it does not substantially deform from an applied force.

In one embodiment, the device 100 can be used for isolating the splenic artery away from the pancreas. In laparoscopic procedures, after the target biological structure, e.g., splenic artery, is separated from the pancreas, there is a space, e.g., about 3 mm to 12 mm, between the target biological structure and the pancreas. When inserting a medical tool in the space between the target biological structure and the pancreas, the medical tool may contact the surrounding biological structures and cause damage. In this respect, the device 100 can operate as a backing plate underneath the target biological structure. This allows the user to exert a force on the device 100 to bias force away from target biological structure or surrounding structures. The device 100 distributes a portion of the force onto the structure below the target biological structure, e.g., the pancreas. After the procedure is over, the device 100 can be withdrawn from the area, such that it is no longer supporting the splenic artery. The device 100 can then be removed from the patient via the incision.

Inflatable Device

Figure 3:
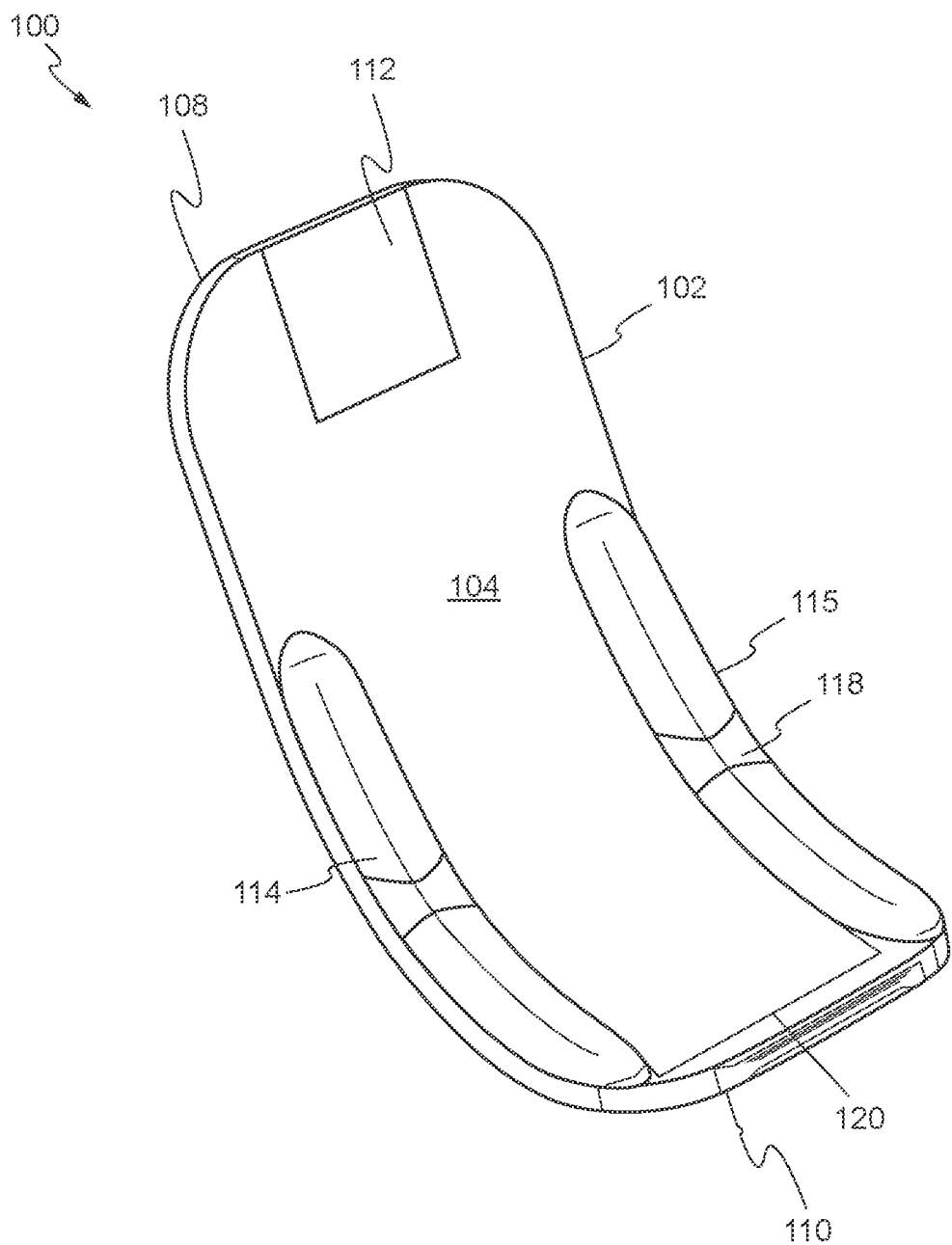
FIG. 3 shows a perspective view of a device, in a first state, according to another embodiment of the present invention.

In another embodiment, the device may include one or more balloons disposed on the main body that are configured to transition the device between a first state and a second state. For example, FIG. 3 shows the device, in a first state, according to one embodiment. In this embodiment, the device 100 isolates and supports a target biological structure away from surrounding structures. As described above, the device 100 may comprise a main body 102 including a front face 104, a rear face 106, a proximal end 108, and a distal end 110.

In this embodiment, the device 100 includes one or more balloons 114, 115 disposed on the distal end 110 of the main body 102. In some embodiments, the one or more balloons 114, 115 are disposed in a position lateral to the main body 102. In a first state, the one or more balloons 114, 115 are deflated. In this configuration, the distal end 110 is substantially arcuate. In some embodiments, each balloon of the one or more balloons 114, 115 includes a recess 118 on a portion of a surface of the balloon that is opposing the front face 104 of the main body 102. The recess 118 provides a space for retaining the target biological structure on the device 100, above the front face 104 of the main body 102.

Figure 4:
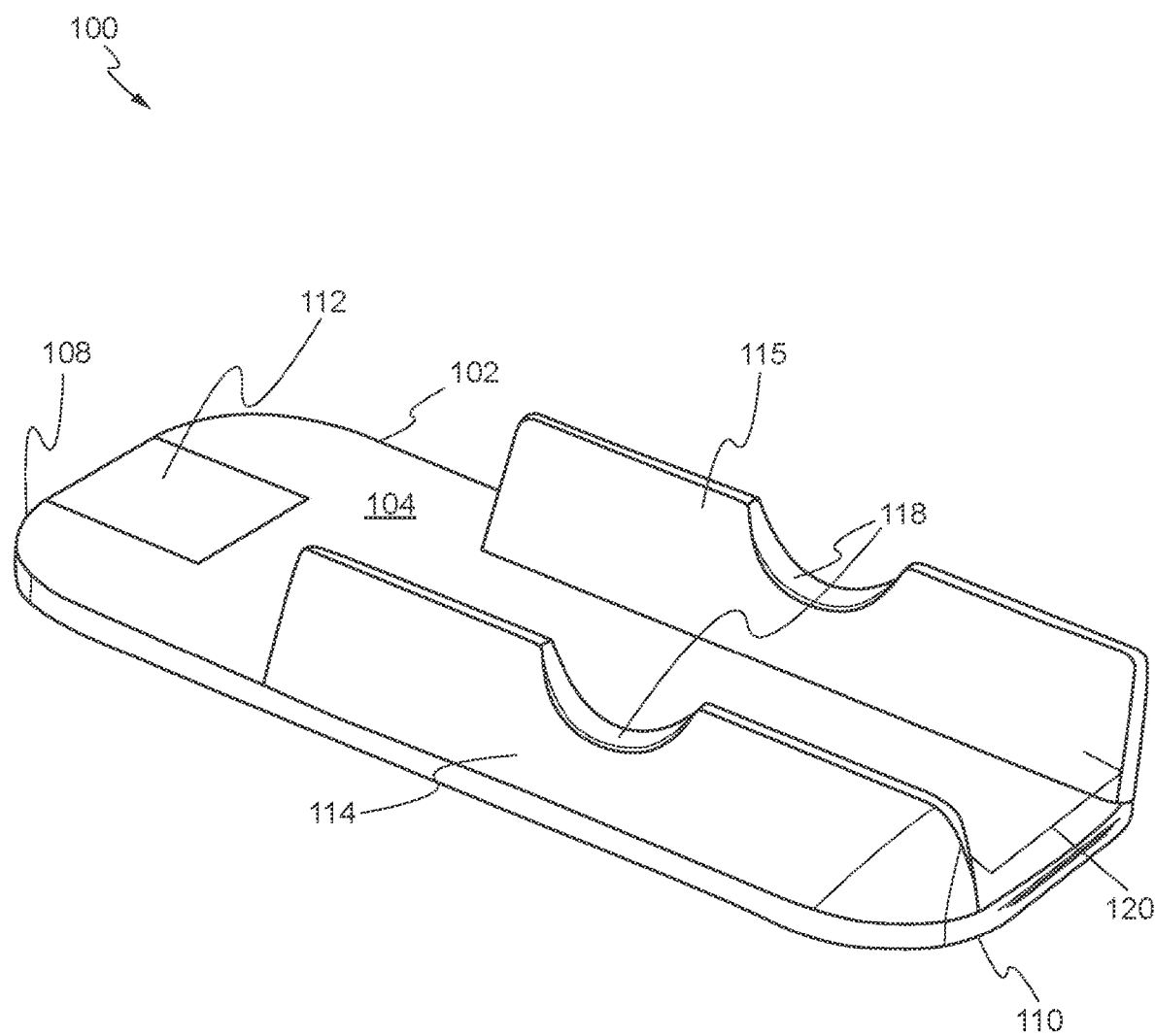
FIG. 4 shows a perspective view of the device, in a second state, according one embodiment of the present invention.

FIG. 4 shows the device, in a second state, according to one embodiment. In the second state, the one or more balloons 114, 115 are inflated (described below). The distal end 110 of the main body 102 is configured to deform to be substantially planar when each of the one or more balloons 114, 115 is inflated. As the one or more balloons 114, 115 are inflated, the increased pressure from the one or more balloons 114, 115 applies a force sufficient to flatten the distal end 110 of the main body 102. For example, the one or more balloons are inflated to a pressure that flattens the distal end 110 to a substantially planar, flat position that is flush with the proximal end 108. In another embodiment, the distal end 110 of the main body 102 is deformed, but may still have some curvature.

In some embodiments, the device 100 includes one or more channels that attach each of the one or more balloons 114, 115 to an inflation control configured to inflate the one or more balloons. For example, the channel can be a thin catheter tube that can supply a fluid to the one or more balloons 114, 115 via a pump or syringe. In some embodiments, a bifurcated catheter tube ("Y-tube") can be attached to each of the one or more balloons with a lower fitting. The distal end of the catheter tube can be attached to the one or more balloons 114, 115 and the proximal end of the catheter tube can be attached to a pump or fluid filled syringe. The pump or syringe can inflate the one or more balloons 114, 115 by filling it with fluid to a desired degree of expansion or pressure and then deflate the balloon by withdrawing the fluid.

In some embodiments, the one or more balloons 114, 115 are angioplasty balloons made of relatively strong but generally elastic material that can be folded into a compact, small diameter cross section. Due to the need for strength and stiffness, the one or more balloons 114, 115 may be rated to high pressures, depending on the diameter. In other embodiments, the one or more balloons 114, 115 comprise soft, very elastic material (e.g., natural rubber latex) as the balloon. Latex and other highly elastic materials generally will expand continuously upon increased internal pressure until the material bursts. As a result, these balloons are generally rated by volume in order to properly distend to a desired size. Although relatively weak, these balloons do have the advantage that they tend to readily return to their initial size and dimensions following inflation and subsequent deflation. It is also contemplated that the balloons can also be made of any medical grade balloon materials, for example, polyurethane or polyethylene terephthalate. In some embodiments, the one or more balloons 114, 115 are relatively small, e.g., a diameter in a range from 1 mm to 5 mm and a length in a range from 5 mm to 30 mm.

In some embodiments, each of the one or more balloons 114, 115 is provided in an elastic cover. When each of the one or more balloons 114, 115 is inflated in the second state, the elastic cover expands to the size of the balloon. During inflation, the one or more balloons 114, 115 exert a force to deform the distal end of the main body 102. In some embodiments, inflating the one or more balloons 114, 115 deform the distal end 110 of the main body 102 from an arcuate configuration to a substantially flat, planar configuration.

Figure 5:
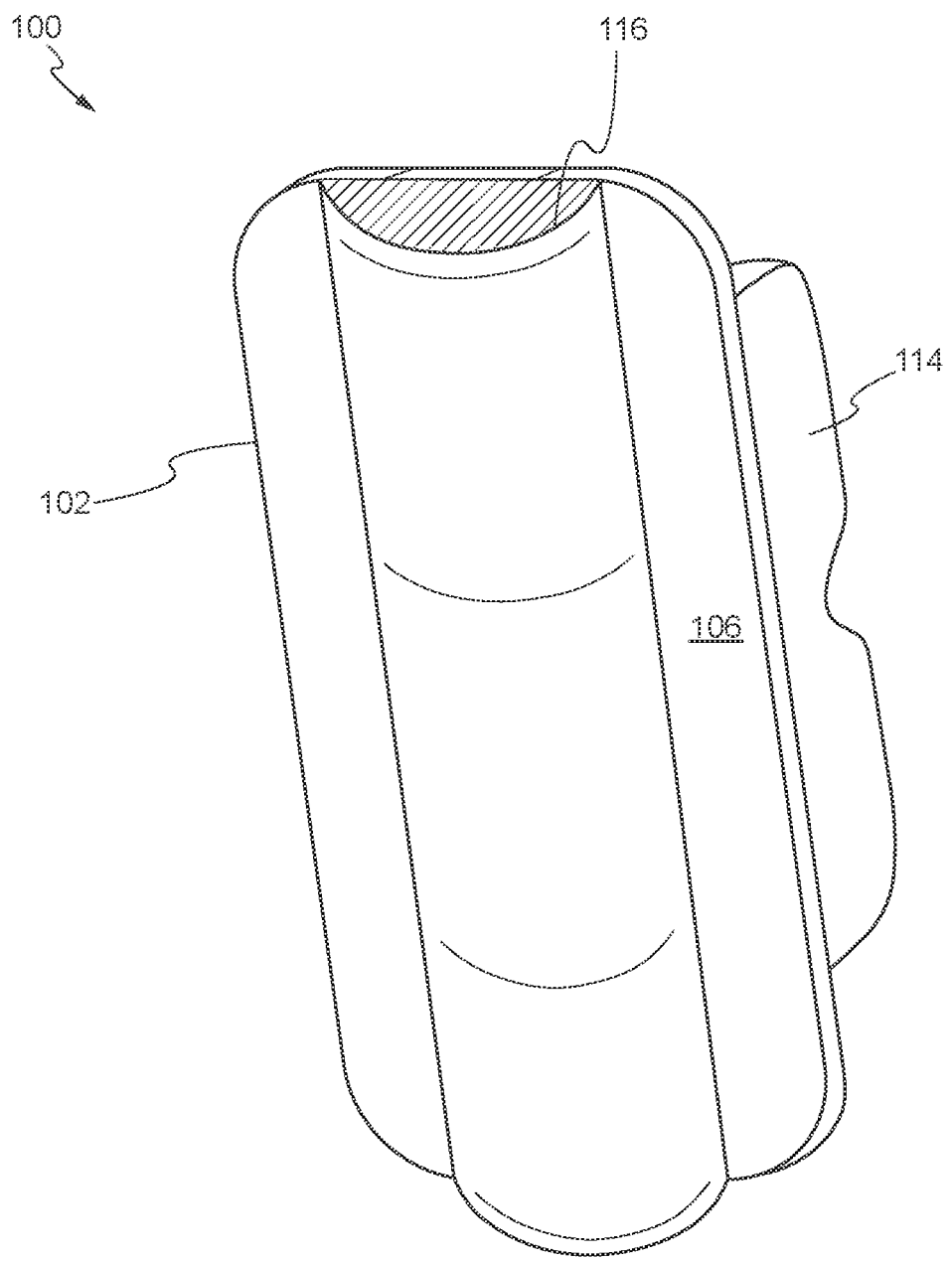
FIG. 5 shows a rear perspective view of the device, in a second state, according another embodiment of the present invention.

FIG. 5 shows a rear perspective view of the device, in a second state, according to one embodiment. In some embodiments, the rear face 106 of the main body 102 includes an additional balloon 116. The additional balloon 116 may be a hemostatic balloon. In some embodiments, the additional balloon 116 is deflated in the first state and is inflated in the second state. During surgery, if any bleeding occurs, the additional balloon 116 can apply a pressure to staunch any bleeding. In this respect, the additional balloon 116 can be selectively inflated and deflated during laparoscopic procedures. After bleeding has stopped, the additional balloon 116 can be deflated. The additional balloon 116 can also include a channel that attaches to an inflation control as described above. In some embodiments, the channel for the additional balloon 115 is separate from the channel of the one or more balloons 114, 115. The additional balloon 116 can be independently inflated via the inflation control.

Figure 6:
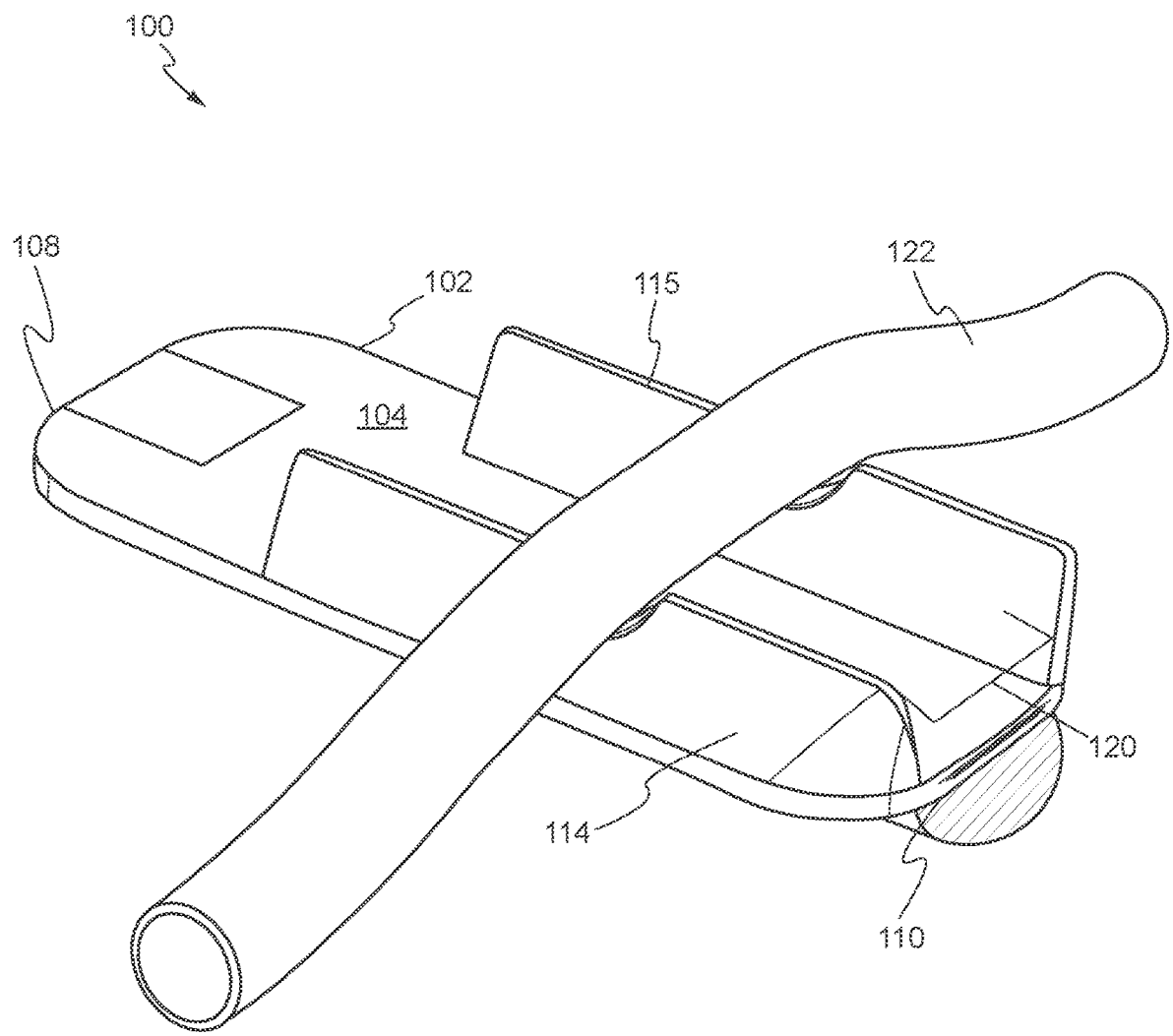
FIG. 6 shows the device supporting a target biological structure according one embodiment of the present invention.

FIG. 6 shows a target biological structure supported on the device according to one embodiment. In one embodiment, the one or more balloons 114, 115 comprise a first balloon 114 on a first side of the main body 102 and a second balloon 115 on a second side of the main body 102. The first side and the second side are edges between the proximal end 108 and the distal end 110 of the main body 102. In the second state, a channel 120 exists between the first balloon 114 and the second balloon 115. In the second state, the first balloon 114 and the second balloon 115 support a target biological structure 122 above the front face 104 of the main body 102. The channel 120 is located below the target biological structure 122 to allow a tool to access the target biological structure from multiple directions.

In Use

In one embodiment, a method for partly isolating a target biological structure is provided. The method may include making an incision in a patient. In some embodiments, the incision is a laparoscopic incision in the abdominal area of a patient. In use, the device may be introduced into the abdominal cavity of a patient through an incision or, alternatively, through a trocar or cannula device which is inserted into the incision for keeping the incision open.

After an incision is made, a device, in the first state, is inserted through the incision to access the target biological structure. For example, the device can be inserted through the incision by threading the device over a guidewire to the target biological structure. In some embodiments, the device may be a device having one or more of the characteristics described above. For example, the device may include a main body and one or more balloons disposed on a distal end of the main body. The main body may include a front face and a rear face having proximal and distal ends. The distal end of the device may have a first state and a second where the distal end is arcuate in a first state and is substantially planar in a second state. In a first state, each of the one or more balloons may be deflated. In a second state, each of the one or more balloons may be inflated. The distal end of the main body is configured to deform to be substantially planar when each of the one or more balloons on the front face are inflated in the second state.

After the device is inserted through the incision, the device is at least partially positioned beneath a target biological structure in the patient. For example, the distal end is positioned beneath the target biological structure. The device is then transitioned from the first state to the second state by at least partly inflating each of the one or more balloons. The inflation of the one or more balloons applies a pressure to the distal end which flattens the distal end to substantially planar configuration that may be flush with a planar proximal end. After inflation, the target biological structure is at least partly supported by each of the one or more balloons. In some embodiments, the transition from the first state to the second state is further caused by inflating an additional balloon disposed on a rear face of the main body, wherein the additional balloon is a hemostatic balloon. In some embodiments, the hemostatic balloon is inflated before each of the one or more balloons.

In some embodiments, the one or more balloons comprises a first balloon on a first side of the main body and a second balloon on a second side of the main body. The first side and the second side are between the proximal end and the distal end of the main body. In the second state, a channel exists between the first balloon and the second balloon. The target biological structure may be supported on the first balloon and the second balloon above the channel. In some embodiments, the method may further include inserting a tool in the channel for accessing the target biological structure.

In some embodiments, the device can remain substantially firm at room temperature, and its insertion through the incision or the trocar is smooth and unobstructed. However, once the device is inserted into the abdomen, the flexible thermoplastic material of the device may become more susceptible to deforming. The change in rigidity of the device may be due to the relationship between properties of the material comprising the device, e.g., glass transition temperature, and the body temperature of the patient. In this regard, if the device is formed of PEEK plastic which has a relatively high glass transition temperature, this can be avoided.

According to this embodiment, the device, in a first a state, may be inserted into a patient's abdomen through a small incision. Then, when the device is positioned near the target biological structure, the balloons of the device can be in inflated in the second state. In the second state, the balloons on the main body are inflated and functions to both isolate and support the target biological structure thereon. Finally, the balloons can be deflated back to the first state and removed via the incision.

In use, the device isolates and positions a target biological structure. In the second state, the one or more balloons function to flatten the distal end of the device. The one or more balloons elevate the target biological structure above the front face of the main body and provides a channel below the target biological structure. The rear face includes a hemostatic balloon to provide pressure around the retractor body to stanch bleeding from surrounding structures.

It is recognized that the devices may be constructed in a number of configurations, which satisfy the primary objective of providing an inflatable, atraumatic laparoscopic device. The devices described above may be used in a wide variety of applications using traditional trocar and cannula designs which range from about 5-12 mm. Of course, the dimensions of the device and the specific shape of the devices, including the balloons, may be specially adapted to address particular circumstances.

Rigid Device

Figure 7:
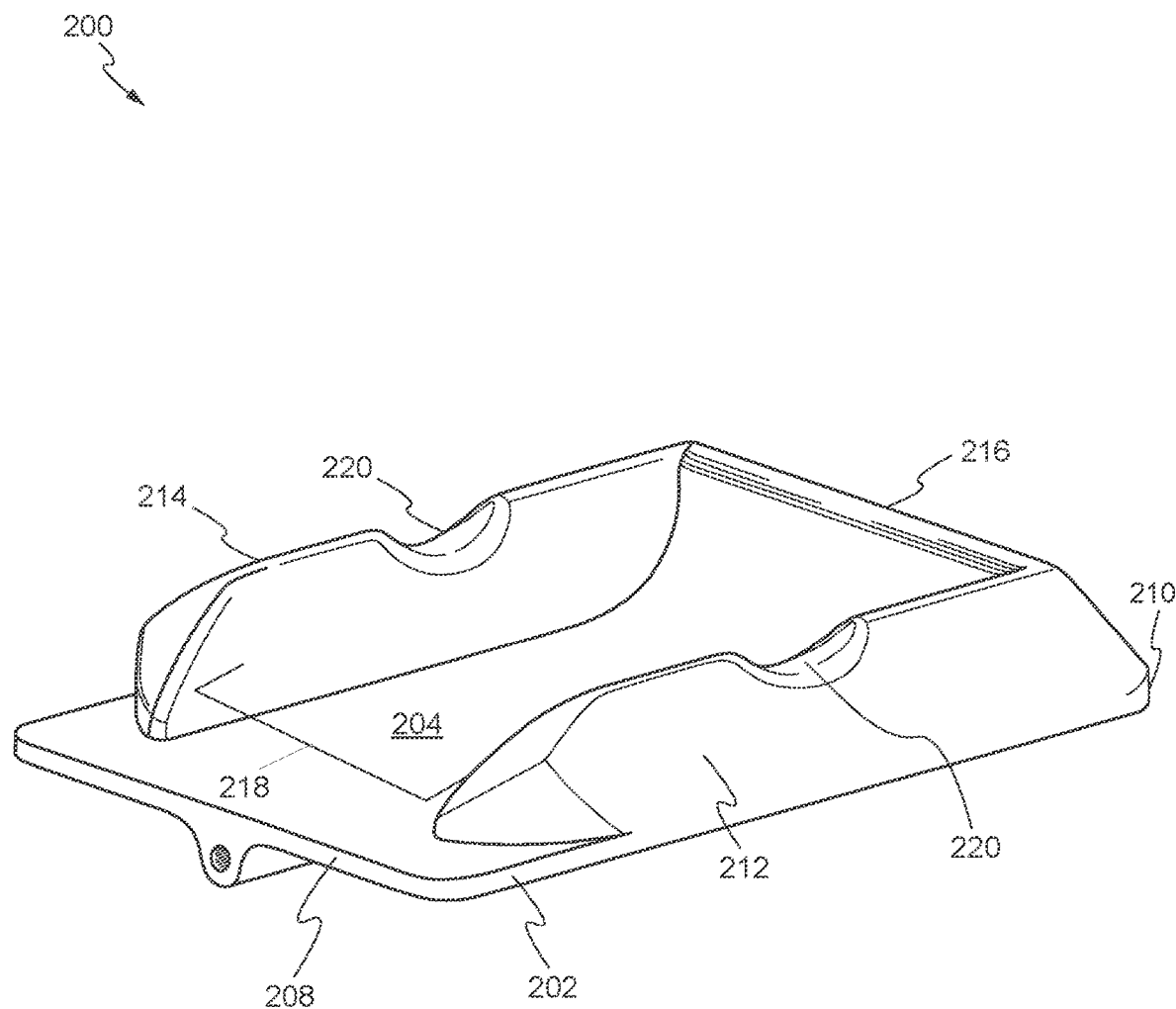
FIG. 7 shows a front perspective view of a device according to another embodiment of the present invention.
Figure 8:
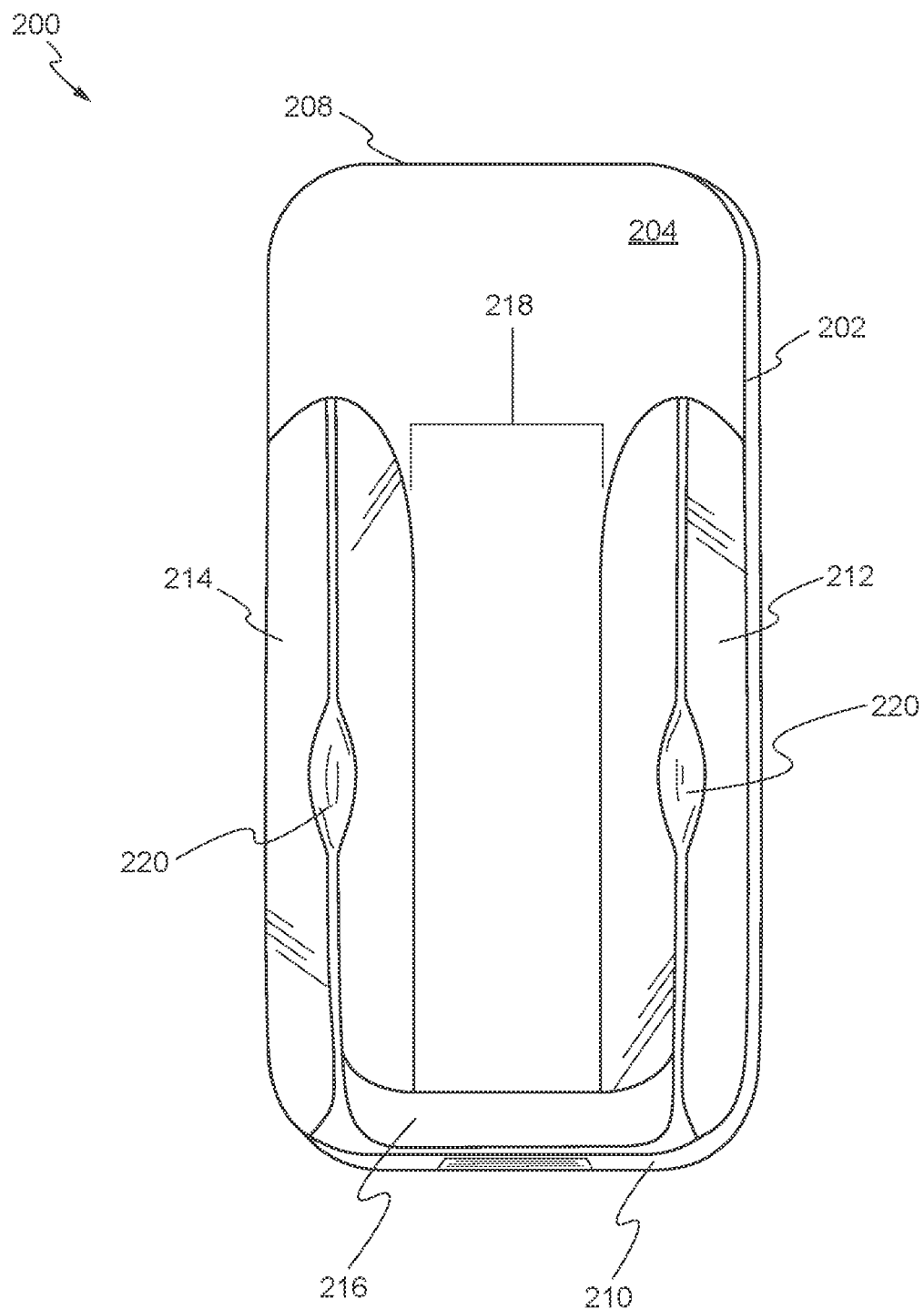
FIG. 8 shows an overhead view of the device according to one embodiment of the present invention.

FIGS. 7 and 8 show front and overhead views of a device, respectively, according to another embodiment. The device 200 comprises a base plate 202 including a front face 204, a rear face 206, a proximal end 208, and a distal end 210. On the front face 204 of the base plate 202, a first sidewall 212 is disposed on a first end and a second sidewall 214 is disposed on an opposing second end. In some embodiments, the device 200 comprises a single, unitary structure formed of a thermoplastic material (as described above). In other embodiments, the device 200 is formed of a rigid material that does not deform.

The device 200 further includes an end wall 216 on the distal end 210 of the base plate 202. In some embodiments, the end wall 216 is on the distal end 210 of the base plate 202 between the first sidewall 212 and the second sidewall 214. The end wall 216 is inclined relative to the proximal end 208 of the base plate 202. The proximal end 208 of the base plate 202 is substantially planar. In some embodiments, the end wall 216 has an incline of at least 30 degrees or more relative to the proximal end 208, e.g., 40 degrees or more, 50 degrees or more, 60 degrees or more, 70 degrees or more, 80 degrees or more, or 90 degrees or more. In some embodiments, the end wall 216 may have an arcuate curvature. The end wall 216 spans the width of the base plate 202 and bridges the first sidewall 212 and the second sidewall 214 at the distal end 210 of the base plate 202.

The first sidewall 212 and the second sidewall 214 form a channel 218 therebetween. The channel 218 is a region between the sidewalls that provides access to the target biological structure. In some embodiments, the first sidewall 212 and the second sidewall 214 each include a recess 220 on a portion of a surface of each of the first sidewall 212 and the second sidewall 214 that is opposing the front face 204 of the base plate 202. The recess 220 is configured to isolate and support the target biological structure above the channel 218. The target biological structure can be a vessel, artery, nerve, tissue or organ of the patient.

In some embodiments, a proximal end of the first sidewall 212 and the second sidewall 214 is approximately normal to the proximal end 208 of the base plate 202. The proximal end of the first sidewall 212 and the second sidewall 214 may each comprise a nose-like structure, e.g., a rounded projection, to separate tissues and other vasculature from the target biological structure. The proximal end 208 of the base plate 202 is substantially planar. In some embodiments, the device 200 may include a handle on the proximal end 208 of the base plate 202. For example, the handle may be a grasper configured to be grasped by Maryland forceps.

Figure 9:
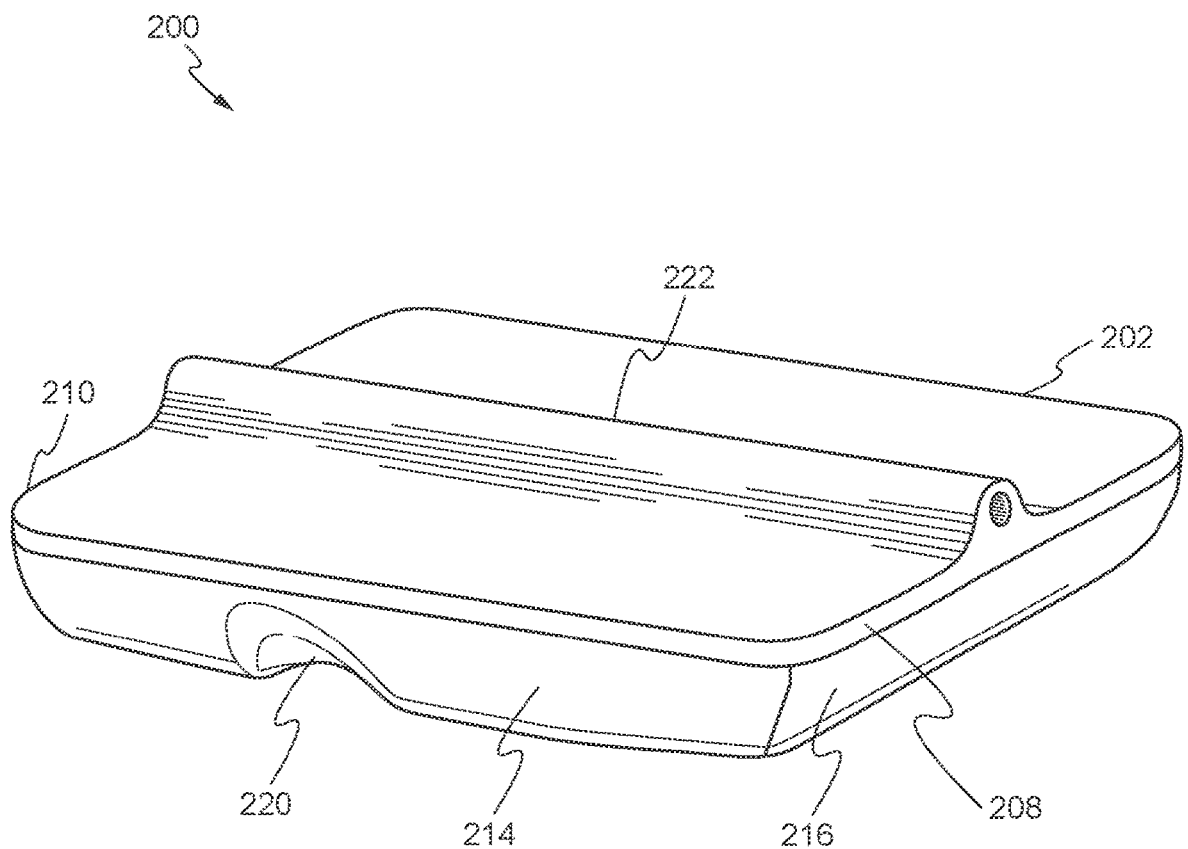
FIG. 9 shows a rear perspective view of the device according to one embodiment of the present invention.

FIG. 9 shows a rear perspective view of the device according to another embodiment. As shown in FIG. 9, the device 200 may further comprise a conduit 222 on the rear face 206 of the base plate 202. The conduit 222 may extend the entire length of the base plate 202. The conduit 222 is configured to receive a guidewire therethrough. As such, the device 200 can be threaded over the guidewire to a target biological structure.

In one embodiment, a method for partly isolating a target biological structure is provided. The method may include making an incision in a patient. In use, the device may be introduced into the abdominal cavity of a patient through a laparoscopic incision or, alternatively, through a trocar or cannula device which is inserted into the incision in the patient's body.

After an incision is made, a device is inserted through the incision to access the target biological structure. In some embodiments, the rear face of the base plate comprises a conduit configured to receive the guidewire. In this way, the device can be inserted through the incision by threading the device over a guidewire to the target biological structure. In some embodiments, the device includes: a base plate comprising a front face and a rear face, the base plate having proximal and distal ends; a first sidewall positioned on a first end of the front face and a second sidewall disposed on an opposing second end of the front face, wherein a channel exists between the first sidewall and the second sidewall; and an end wall positioned on the distal end of the main body between the first sidewall and the second sidewall. The end wall is inclined relative to the proximal end of the base plate.

After the device is inserted through the incision, the device is positioned at least partially beneath a target biological structure in the patient. The target biological structure is supported on the first sidewall and second sidewall above the base plate. In some embodiments, the first sidewall and the second sidewall include a recess for isolating the target biological structure above a channel formed between the sidewalls. A user can insert a tool in the channel to access the target biological structure. In some embodiments, the angle of the tool can be adjusted by contacting the tool with the end wall.

The design of each of the devices advantageously allows a user to partly isolate a target biological structure and more easily access all areas of the target biological structure from multiple directions. In this way, during laparoscopic procedures, a user can modify, e.g., ligate, incise, or attach tools, to target biological structures. The device advantageously allows a user to separate tissue and surrounding structures from the target biological structure, position and retain a target biological structure, create a working space underneath and around the target biological structure, and an end wall for turnaround of surgical tools.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that embodiments of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art.

I claim:

1. A device for partly isolating a target biological structure in a patient, the device comprising:
    a main body comprising a front face and a rear face, the main body having a proximal end and a distal end, wherein a first region of the main body adjacent the distal end is arcuate in a first state and is substantially planar in a second state, wherein, in the first state, the first region is arcuate by a curvature transverse to a longitudinal axis of a second region of the main body adjacent the proximal end;
    one or more balloons, each balloon of the one or more balloons being disposed on a front face of main body at the first region of the main body adjacent the distal end; and
    an additional balloon disposed on the rear face of the main body,
    wherein each of the one or more balloons is deflated in the first state,
    wherein each of the one or more balloons is inflated in the second state, wherein the first region of the main body adjacent the distal end is configured to deform to be substantially planar when each of the one or more balloons are inflated in the second state.

2. The device of claim 1, wherein the second region of the main body adjacent the proximal end of the main body is substantially planar.

3. The device of claim 1, wherein the additional balloon is a hemostatic balloon.

4. The device of claim 1, wherein the additional balloon is deflated in the first state and is inflated in the second state.

5. The device of claim 1, further comprising one or more channels that attach each of the one or more balloons and the additional balloon to an inflation control configured to inflate the one or more balloons and the additional balloon.

6. The device of claim 1, wherein the one or more balloons comprise a first balloon on a first side of the front face of the main body adjacent the distal end and a second balloon on a second side of the front face of the main body adjacent the distal end, wherein the first side and the second side are between the proximal end and the distal end on the front face of the main body.

7. The device of claim 6, wherein, in the second state, a receiving channel on the front face of the main body exists between the first balloon and the second balloon.

8. The device of claim 7, wherein, in the second state, the first balloon and the second balloon support a target biological structure above the front face of the main body, and wherein the receiving channel is located below the target biological structure.

9. The device of claim 8, wherein the target biological structure is a vessel, artery, nerve, or organ of the patient.

10. The device of claim 1, wherein, in the second state, each balloon of the one or more balloons includes a recess on a portion of a surface of the balloon that is opposing the front face of the main body.

11. The device of claim 1, wherein the main body comprises a flexible thermoplastic material.

12. The device of claim 1, further comprising a handle on the first region of the main body adjacent the proximal end.

13. A method comprising:
    making an incision in a patient;
    inserting a device, in a first state, to access a target biological structure in the patient through the incision, the device comprising:
        a main body comprising a front face and a rear face, the main body having a proximal end and a distal end, wherein a first region of the main body adjacent the distal end is arcuate in a first state and is substantially planar in a second state, wherein, in the first state, the first region is arcuate by a curvature transverse to a longitudinal axis of a second region of the main body adjacent the proximal end; and one or more balloons, each balloon of the one or more balloons being disposed on a front face of main body at the first region of the main body adjacent the distal, and an additional balloon disposed on the rear face of the main body;

wherein each of the one or more balloons is deflated in the first state, wherein each of the one or more balloons is inflated in the second state, wherein the first region of the main body adjacent the distal end is configured to deform to be substantially planar when each of the one or more balloons are inflated in the second state;

positioning the device at least partially beneath a target biological structure in the patient; and transitioning the device from the first state to the second state at least partly by inflating each of the one or more balloons, wherein the inflation causes the target biological structure to be at least partly supported by each of the one or more balloons.

14. The method of claim 13, wherein transitioning the device from the first state to the second state is further caused by inflating the additional balloon disposed on the rear face of the main body, wherein the additional balloon is a hemostatic balloon.

15. The method of claim 14, wherein the hemostatic balloon is inflated before each of the one or more balloons.

16. The method of claim 13, wherein the one or more balloons comprise a first balloon on a first side of the front face of the main body adjacent the distal end and a second balloon on a second side of the front face of the main body adjacent the distal end, wherein the first side and the second side are between the proximal end and the distal end on the front face of the main body.

17. The method of claim 16, wherein, in the second state, a receiving channel on the front face of the main body exists between the first balloon and the second balloon, wherein the target biological structure is supported on the first balloon and the second balloon above the receiving channel.

18. The method of claim 17, further comprising inserting a tool in the receiving channel for accessing the target biological structure.

19. The method of claim 13, wherein the inserting step comprises threading the device over a guidewire to the target biological structure.

* * * * *